United States Patent [19]

Tsao et al.

[11] 4,063,017

[45] Dec. 13, 1977

[54] POROUS CELLULOSE BEADS AND THE IMMOBILIZATION OF ENZYMES THEREWITH

[75] Inventors: George T. Tsao; Li Fu Chen, both of West Lafayette, Ind.

[73] Assignee: Purdue Research Foundation, West Lafayette, Ind.

[21] Appl. No.: 679,497

[22] Filed: Apr. 22, 1976

[51] Int. Cl.² .................... C08B 15/10; C08B 16/00
[52] U.S. Cl. ........................ 536/57; 195/63; 195/DIG. 11; 260/13; 264/13; 264/14; 536/80
[58] Field of Search ................ 195/63, DIG. 11; 264/13-15; 536/57, 80, 98, 99

[56] References Cited

U.S. PATENT DOCUMENTS

| | | | |
|---|---|---|---|
| 2,118,663 | 5/1938 | Bradshaw | 536/89 |
| 2,543,928 | 3/1951 | O'Neill et al. | 264/13 |
| 2,773,027 | 12/1956 | Powers | 264/13 |
| 2,843,583 | 7/1958 | Voris | 106/170 |
| 3,236,669 | 2/1966 | Williams | 106/311 |
| 3,251,824 | 5/1966 | Battista | 536/89 |
| 3,501,419 | 3/1970 | Bridgeford | 536/57 |
| 3,505,299 | 4/1970 | Baker et al. | 528/496 |
| 3,573,277 | 3/1971 | Grant | 536/57 |
| 3,739,049 | 6/1973 | Honjo | 264/13 |
| 3,746,621 | 7/1973 | Kondo et al. | 195/63 |
| 3,905,954 | 9/1975 | Jones et al. | 264/191 |
| 3,936,441 | 2/1976 | Holst et al. | 536/98 |
| 3,947,325 | 3/1976 | Dinelli et al. | 195/63 |

OTHER PUBLICATIONS

Tsumura et al., "Continuous Isomerization of Glucose by a Column of Glucose Isomerase", Journal of Food Science and Technology, vol. 14, No. 12, pp. 539-540 (1967).

Primary Examiner—Ronald W. Griffin
Attorney, Agent, or Firm—Cushman, Darby & Cushman

[57] ABSTRACT

Porous cellulose beads are prepared by distributing droplets of a solvent mixture containing a cellulose derivative into an aqueous solution to form porous beads which are then washed and hydrolyzed to form porous cellulose beads. The porous cellulose beads, which may be cross-linked, if desired, by suitable treatment, are useful carriers to which enzymes can be immobilized.

22 Claims, 3 Drawing Figures

POROUS CELLULOSE BEADS AND THE IMMOBILIZATION OF ENZYMES THEREWITH

BACKGROUND OF THE INVENTION

Porous cellulose beads provide a relatively low-cost, stable material possessing versatile chemical properties such that they can be useful as a carrier for immobilized enzymes and other active biological agents.

While ordinary cellulose particles and regenerated cellulose powders meet most of the desired requirements of good carriers to which enzymes can be immobilized, they suffer from configural disadvantages which cause column reactors to become tightly packed resulting in reduction of flow and, therefore, insufficient contact time between the immobilized enzyme and reaction fluid. The immobilization of enzymes on an insoluble carrier is a widely-accepted technique of applying enzymes for a practical application, avoiding the necessity of employing fresh enzymes for each desired use. Through immobilization of the enzyme, stabilization is achieved which provides for efficient enzyme use and provides for the design and operation of enzyme reactors in a continuous mode.

To a large degree, the success of an immobilized enzyme for use in practical application depends upon the properties of the carriers employed for immobilization. Accordingly, a good carrier should meet the requirements of being inexpensive and should be of such a physical shape that it is easy to be employed in reactors. In this regard, the shape of a spherical bead is particularly desirable, since it is useful in a packed bed, fluidized bed, expanded bed, stirred tank, or other common types of chemical reactor designs. Such a carrier should also have the proper physical and mechanical strength such that it will not be crushed or deformed when packed in a tall column. Crushing and deformation results in the column becoming tightly packed, thereby blocking the flow of liquid reagents through the column, thus decreasing the efficiency of the chemical reactor. Suitable carriers should also possess versatile chemical properties such that the immobilization of enzymes and other biological agents onto the carrier through ionic or chemical covalent bonding, as well as surface absorption, can be readily achieved. In this regard, the carrier should have a high capacity for forming a large number of bonds such that each unit of the carrier can immobilize large amounts of the enzyme desired. In this regard, a carrier having a high degree of porosity and uniformly distributed internal void spaces is particularly desirable. Such porosity provides for good diffusion of chemical reagents or reaction products into and out of the internal void spaces of the cellulose beads. Carriers should be chemically stable and physically strong, and be made of inert material which resists microbiological attack causing carrier deterioration and will thereby provide an immobilized enzyme system having a prolonged active life.

Currently, porous glass and porous ceramic particles are commonly employed for the immobilization of enzymes and such particles meet most of the above requirements for an acceptable particle, except that they are relatively expensive. Furthermore, the number of chemical reactions which may be used for immobilization of enzymes to glass and ceramic carriers is limited.

In U.S. Pat. Nos. 3,905,954; 3,505,299; 3,501,419; 3,397,198; 3,296,000; 3,236,669; 2,843,583; and 2,465,343, there is described the preparation of a variety of cellulose materials in a variety of forms, some of which are described as suitable for use in fixing biologically-active materials such as enzyme thereto. However, these processes seem to suffer from the disadvantage of being expensive in providing the desired material and generally are of an undesirable physical shape for use in such chemical reactors as packed beds and fluidized beds.

Accordingly, the primary object of the present invention is to provide a means for preparing inexpensive, highly-porous, stable particles having versatile chemical properties whereby they may be useful as a carrier to which enzymes or other biologically-active materials can be immobilized.

A further object of the present invention is to provide a method for the transformation of cellulose derivatives into highly-porous particles having good mechanical stability such that it will provide for adequate passage of liquid therethrough when operated in packed bed reactors.

Still yet another object of the present invention is to provide a porous cellulose bead having sufficiently large surface area to provide high immobilization capacity of enzymes.

Still a further object of the present invention is to provide a porous cellulose bead having improved physical and mechanical strength so that it will not be crushed and deformed when used in chemical reactors.

These and other objects of the present invention will be more fully apparent from the discussion set forth hereinbelow.

DESCRIPTION OF THE INVENTION

According to the present invention, a process is provided for the preparation of porous cellulose beads which are suitable for use as a carrier of enzymes and other biological agents. The invention also provides a means for the modification of the chemical and physical property of porous beads made from cellulose derivatives, as well as techniques for immobilizing enzymes and other biological active agents onto the porous beads so formed. While ordinary microcrystalline cellulose and other particles made from cellulose satisfy many of the general requirements for a suitable carrier of enzymes, such particles suffer from the tendency to pack together tightly under pressure and also fail to provide sufficient porosity to attach a sufficiently-large amount of enzymes thereto. Cellulose derivatives are generally inexpensive and when treated according to our invention provide a highly-versatile material for chemical reactions being generally biologically inert. Thus, the cellulose derivative beads herein provide many desirable properties for use as a carrier of immobilized enzymes.

Our process for the modification of the physical properties of cellulose derivatives, in order to provide porous cellulose beads, involves the steps of:

a. dissolving a cellulose derivative in an inert organic, water-miscible solvent to form a solution having a density greater than that of the precipitation solution as defined hereinbelow;

b. distributing said solution in the form of droplets into a precipitation solution whereby said cellulose derivative is precipitated in the form of porous beads;

c. separating the precipitated beads from said solution;

d. washing the separated porous beads with water;

e. hydrolyzing the washed beads to convert the beads to cellulose and to increase the active sites for attachment of enzymes and other biological agents;

f. washing the hydrolyzed beads to obtain porous cellulose beads.

As used herein, the precipitation solution is defined as a liquid solution which is a non-solvent for the cellulose derivative and is miscible with the above inert organic, water-miscible solvent. By means of illustration, the precipitation solution may be water or an aqueous solution.

As will be apparent from the discussion herein, a number of variations are possible in the above-described process in preparing the desired porous cellulose beads. In addition to cellulose acetate, other cellulose derivatives may be employed as a starting material for the preparation of the porous beads, for example, cellulose nitrate, methyl cellulose and carboxymethyl cellulose. The term "cellulose derivative" as used herein is intended to include materials from which cellulose may be regenerated such as by means of, for example, hydrolysis or hydrogenation.

The organic solvent for the cellulose derivative can vary, but should be chemically inert to the cellulose derivative and wholly or substantially miscible with the precipitation solution. It is of prime importance that the density of the cellulose derivative solution formed by adding the cellulose derivative to the inert solvent be greater than that of the precipitation solution into which it is distributed such that when droplets of the cellulose derivative solution is distributed into the precipitation solution, the droplets will sink when the aqueous solution is not agitated. Suitable solvents include among others, for example, dimethylsulfoxide, acetone or mixtures thereof.

The solution of cellulose derivative and inert solvent should have a controlled cellulose-to-solvent ratio since such will have an effect on the eventual porosity of the beads prepared. Generally, a small ratio (larger content of solvent) results in beads having a larger porosity. A cellulose-to-solvent ratio of from 1:20 to 1:3 (weight-/volume) has been found suitable for preparing cellulose beads having various specific applications. Preferably, a cellulose-to-solvent ratio of 1:10 to 1:6 (weight-/volume) is employed to provide an easy-to-handle solution which results in porous cellulose beads of desirable properties having a void space of at least 50% by volume. Beads having a higher porosity will generally have a larger proportion of uniformly distributed internal void spaces providing less diffusion hindrance, but will be somewhat weaker in physical strength than beads of lower porosity.

The preferred precipitation solution into which the solution of cellulose derivative is to be distributed generally consists of water, but may be an aqueous solution which contains suitable amounts of non-ionic or ionic surfactants to reduce the surface tension thereof and facilitate formation of the porous beads. The precipitation solution can also be non-aqueous so long as the cellulose derivative is insoluble therein and the necessary density requirement is met. Thus, aliphatic hydrocarbon solutions may be used such as pentane, hexane, decane and the like so long as they are liquid in form, possess a density less than that of the inert organic solvent and are miscible therewith. When the cellulose derivative solution is distributed by spraying via a suitable means such as a spray nozzle, the pressure drop and miscibility of the inert solvent in the aqueous solution results in a dispersion and ultimate precipitation of porous beads of the cellulose derivative.

After precipitation of the porous beads, cellulose is regenerated from the derivative by hydrolysis in order to render the bead more insoluble in water, and also to create more active sites for enzyme attachment. In regenerating cellulose from its derivative after formation of the beads, one can remove the substituting groups (such as acetate from cellulose acetate) in order to regenerate all the hydroxyl groups normally present in the cellulose material. The higher the degree of regeneration, the more stability is to be found in the resulting beads. In some cases, wherein enzymes are to be immobilized on the cellulose bead carriers, it is desirable to convert the hydroxy or substituting groups into functional chemical groups, such as amino groups, which facilitate enzyme attachment.

Figure 1:
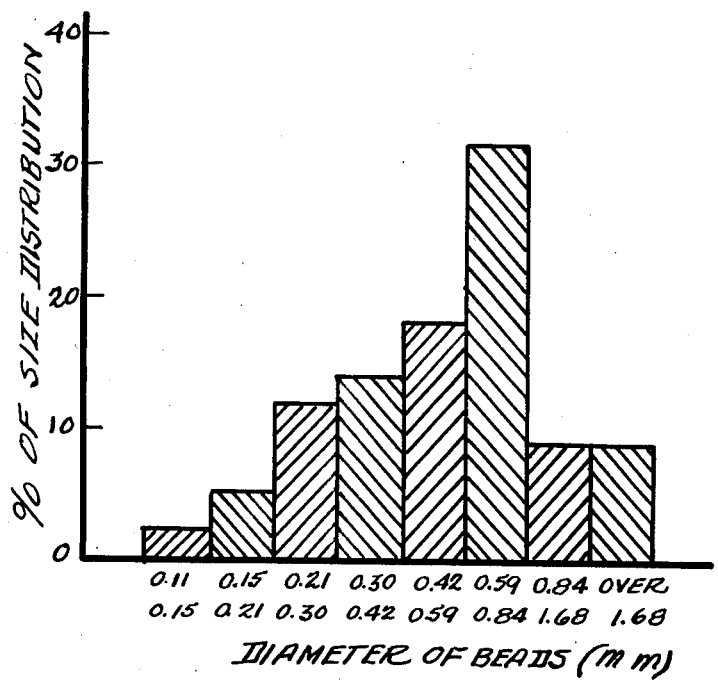
FIG. 1 is an illustration of the pore size distribution of the porous beads.

Reference is made to FIG. 1 which illustrates the size distribution of the final porous beads obtained by distributing (by spraying) a solution of cellulose derivative through a spray nozzle, according to the detailed procedure outlined hereinbelow. Beads which are either too large or too small, depending upon the intended end use, may be collected and re-dissolved in the appropriate solvent, if desired. Generally speaking, if employed in a column type chemical reactor, beads of a uniform size are preferred.

Figure 2:
FIG. 2 is a scanning electromicrograph of a porous cellulose bead.

The porous cellulose beads prepared by the process described above generally have a very high porosity. When a cellulose-to-solvent ratio of 1:10 (weight-/volume) is used in preparing the cellulose/solvent solution, the final beads formed have a high porosity of about 90% void. A scanning electromicrograph of a porous cellulose bead prepared by the process is shown in FIG. 2. From this view, one can observe several important features of the beads produced. Firstly, porous openings are uniformly distributed over the surface of the bead. For most applications, this is desirable because it can provide an immobilized enzyme catalyst of uniform activity. The void phase of the cellulose beads is continuous. This is a desirable feature because a discontinuous, discrete "bubble" would result in useless and non-accessible dead space in an immobilized enzyme system. Thirdly, there is no hard "skin" at the bead surface. This is due to the gentle treatment in the gradual solidification and formation of the beads. A hard skin will cause serious diffusional hindrance. Finally, the pore sizes are quite uniform. As a result, all of the interior surface area of the internal void spaces of the beads will be accessible for enzyme immobilization and for enzyme catalyzed reactions. Both the high porosity and other noted features have made the porous cellulose beads of this invention uniquely suited for use in immobilization of enzymes and other biologically-active agents.

An important property of an enzyme carrier is the pressure drop it causes at various liquid flow rates through an enzyme reactor containing the carrier. For example, DEAE-cellulose is currently used in industry as an enzyme carrier for the conversion of glucose into fructose. For DEAE-cellulose, the pressure drop is very high and consequently only shallow beds can be used to obtain a reasonable rate of fluid flow. The pressure drop characteristics of the porous cellulose beads of this invention in a packed column operation is shown by Curve A in FIG. 3. The nominal linear flow velocity is calculated by dividing the volumetric flow rate of the feed liquid to the column by the column cross-sectional area. In practical operations, the nominal linear flow velocity in industrial column reactors will be less than 0.5 cm/sec. For example, with a reactor column of two feet (60.96 cm) inside diameter, a linear velocity of 0.5 cm/sec is equivalent to a volumetric flow rate of 1389 gal/hr (5254 liters/hr). In a typical industrial operation for producing fructose from glucose, the sugar concentration in the feed is about 5 lb. sugar/gallon. The above flow rate will yield more than 60 million pounds of the product per 2 feet column per year. Because of the residence time requirement of the enzymatic reaction, the linear flow rate is usually less than 0.5 cm/sec. Therefore, it can be seen that the porous cellulose beads of this invention do not pose any serious engineering problems with regard to pressure drop, when used in column type chemical reactors as a carrier to which enzymes and other biologically-active agents can be immobilized.

Figure 3:
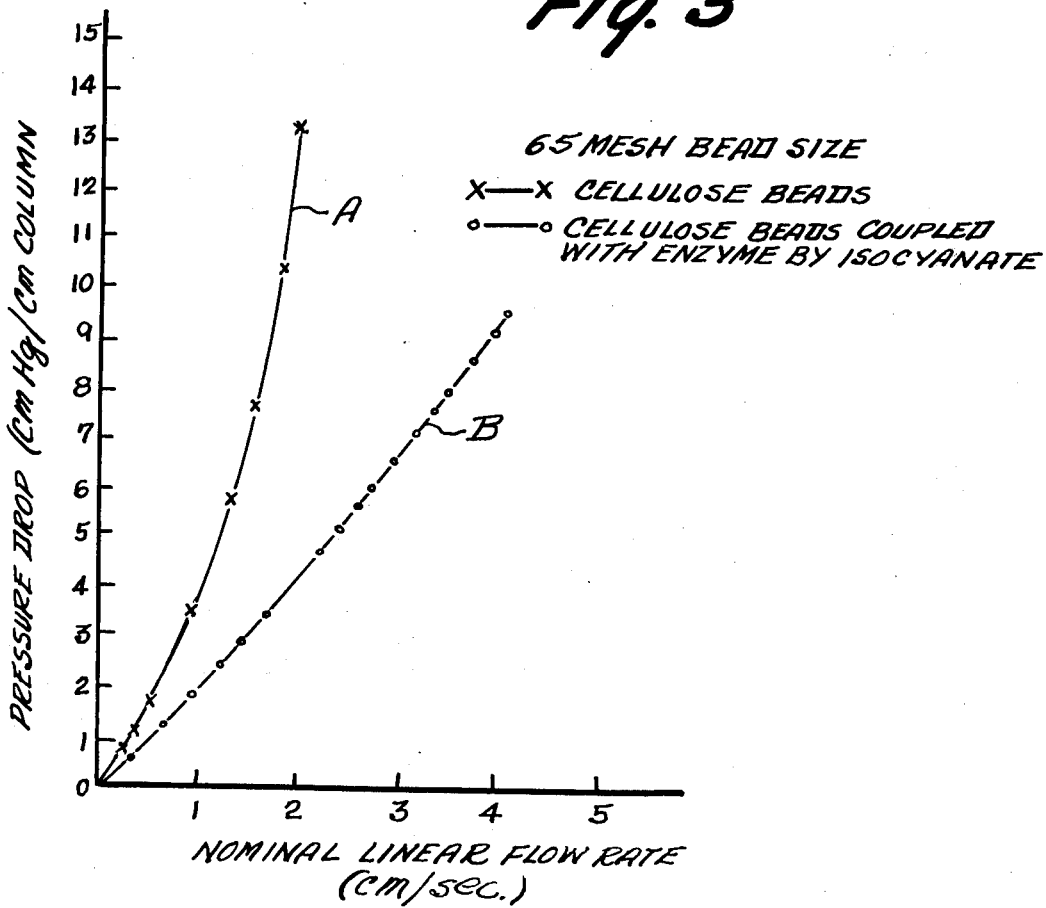
FIG. 3 is a plot of the pressure-drop characteristics of the porous cellulose beads.

The flow characteristics and other physical and mechanical properties of the porous cellulose beads can be improved by cross-linking with bi- and/or multi-functional compounds. Curve B in FIG. 3 shows the pressure drop requirement of the porous cellulose beads after the treatment with tolylene-2,4-diisocyanate and enzyme immobilization. Above a nominal linear velocity of 2 cm/sec, the untreated cellulose beads (Curve A) become compressed and deformed considerably, resulting in a drastic increase of the pressure drop. Curve B concaves upward only slightly indicating little deformation, if any, of the treated beads.

Treatment of the porous cellulose beads with a cross-linking agent, either before or after hydrolysis of the beads, results in an increase of their physical strength. Attachment of enzymes onto the beads will also increase their physical strength. After treatment with, for example, a diisocyanate (e.g., tolylene-2,4-diisocyanate or hexamethylene diisocyanate), the beads in fact become quite rigid and strong. Cross-linking with epichlorohydrin also improves the physical properties of the porous cellulose beads. The chemistry of cross-linking of polysaccharides, including cellulose and starch, is a well-developed branch of physical science. Other suitable cross-linking agents among others include formaldehyde in hydrochloric acid solution or glutaraldehyde. Many other carbohydrate cross-linking agents are well known, as shown, for example, by Jones et al., U.S. Pat. No. 3,905,954.

In general, the porous beads of the present invention are prepared according to the following steps:

a. a hydrolyzable form of cellulose is dissolved in an inert organic water-miscible solvent in a controlled ratio of cellulose derivative-to-solvent which is generally in the range of 1:20 to 1:3. The solvent should be wholly or substantially miscible with the precipitation solution and the density of the cellulose solution should be sufficiently great such that upon contact with the precipitation solution, the solvent becomes readily miscible with the precipitation solution and cellulose derivative precipitates therein. If desired, the cellulose derivative solution may contain a surfactant.

b. a cellulose-derivative solution is distributed (e.g., by spraying) in the form of droplets into a precipitation solution. Upon contact with the precitpation solution, which may contain a surfactant, the solvent is dispersed within the solution media and porous beads of the cellulose material gradually form as they precipitate to the bottom of the tank holding the precipitation solution. The cellulose derivative solution may suitably be sprayed under pressure through an atomizing nozzle into a precipitation solution bath. If desired, the bath may be agitated to enhance the formation of the beads.

c. the precipitated beads, after being washed, are then hydrolyzed in order to regenerate cellulose, thereby providing a porous cellulose bead having active sites for enzyme attachment. If desired, in order to increase the stability of the porous beads or provide suitable reaction sites, one can chemically modify the beads in a number of ways. For example, the beads may be cross-linked in order to provide greater stability and increased physical strength. Also, one can chemically substitute either positively-charged or negatively-charged groups to alter the surface-adsorption properties of the cellulose bead. The cellulose itself is generally hydrophilic and, thus, by altering the reaction sites thereof, one can alter its hydrophilic properties.

The present invention further provides for a method by which enzymes and other biological active agents may be immobilized by attachment onto the porous cellulose beads described hereinbefore. For example, one may convert porous cellulose beads, as described above, to diethylaminoethyl (DEAE) cellulose by reacting said beads with N,N-diethyl 2-chloroethylamine hydrochloride in a conventional manner. Beads so obtained contain DEAE-cellulose and were successfully used to attach glucose isomerase, derived from a streptomyces culture. We have also employed a procedure involving cyanogen bromide to immobilize the glucose isomerase.

Another procedure for enzyme immobilization on the porous cellulose beads involves the use of tolylene-2,4-diisocyanate. Diisocyanate was employed to cross-link cellulose to improve the physical strength of the porous beads. However, we have found that the porous cellulose beads of the present invention when treated with diisocyanate, can immobilize enzymes on the surface thereof by simply mixing the diisocyanate-treated beads together with an enzyme solution. For example, when glucoamylase was used, the diisocyanate beads attached more than 1000 international units of the enzyme per gram of dry beads. While not wishing to be limited in any way by the following theory, it appears that when dry porous cellulose beads are in dry acetone with tolylene-2,4-diisocyanate in the presence of a catalyst (for example, triethylamine), a considerable degree of cross-linking occurs between cellulose molecules in light of the improved physical strength of the beads. After a sufficient length of time for reaction, the beads were washed with dry acetone to remove free diisocyanate residues. The cellulose beads appear to possess a large number of attached isocyanate groups. Upon mixing the treated beads with an aqueous enzyme solution, enzyme molecules appear to be covalently bonded to the cellulose beads through the isocyanate groups. It has also been found that washing the treated beads with water results in converting isocyanate groups to amino groups. In such a manner, we were successful in immobilizing an enzyme, glucoamylase, to the amino cellulose beads with glutaraldehyde, an agent well known for its capability of reacting and cross-linking amino groups (on the beads and the enzyme).

The following examples are offered to more fully describe the invention, but are not to be construed as limiting the scope thereof:

EXAMPLE I

Fifty (50) grams of cellulose acetate (visc 3 from Eastman Kodak Chemicals) were dissolved in 400 ml of solvent A (composed of acetone and dimethylsulfoxide in a volume ratio of 6-to-4) to form a 12.5% (weight-/volume) solution. With a spray gun (paint sprayer from Sears Roebuck & Co.), the cellulose solution was then sprayed at an air pressure of 20 psi as fine droplets into a water tank containing 40 gallons of water and four drops of common household detergent. Upon contacting the surface of the water, the cellulose acetate droplets coagulate into porous beads and sink to the bottom. The porous beads were then collected and washed. The washed beads were then deacetylated with about a 0.15 N of sodium hydroxide overnight at room temperature. The deacetylated beads were then washed and suction-dried, yielding a porous cellulose bead having a void space greater than 50% by volume ready for use in enzyme immobilization. FIG. 1 illustrates the size distribution of the porous beads obtained.

EXAMPLE II

Using a 10% (weight/volume) cellulose acetate solution in solvent A, according to the process of Example I, porous beads were also formed and were suitable for use in enzyme immobilization.

EXAMPLE III

A 10% (weight/volume) cellulose acetate (visc 3 from Eastman Kodak Chemicals) solution was prepared in solvent B (acetone and formamide in a volume ratio of 7-to-3). The cellulose acetate solution was then sprayed and hydrolyzed according to the procedure in Example I above. Highly porous cellulose beads were obtained having a void space greater than 50% by volume.

EXAMPLE IV

The procedures outlined in Example II, above, were repeated using a solution prepared with cellulose acetate of visc 45 type (available from Eastman Kodak Chemicals). Porous beads were also obtained having excellent properties for enzyme immobilization.

EXAMPLE V

The procedures outlined in Example II, above, were carried out using a 10% weight/volume solution of cellulose triacetate (available from Eastman Kodak Chemicals) in solvent A. The beads resulting therefrom exhibited excellent porosity for enzyme immobilization.

EXAMPLE VI

One (1) gram of porous cellulose beads, produced according to Example I, was dispersed in 15 ml water which was adjusted to pH 11.5 with sodium hydroxide and kept at a constant temperature of 20° C. One (1) gram of cyanogen bromide was added to this dispersion. The pH was maintained at 11.5 with 1 N NaOH. After 15 minutes, the beads were washed with a phosphate buffer (0.1 M) at pH = 7.0 and 0° C. Fifteen (15) ml of glucoamylase solution (30 mg/ml) were then added to the beads. The mixture was left overnight. The beads so prepared contained 1830 units of enzyme activity per gram dry weight of cellulose bead at 60° C. using 5% maltose as substrate. One unit of enzyme activity is defined to be that which produces one micromole of product per minute.

EXAMPLE VII

Porous cellulose beads (0.2 gm), obtained as in Example I, were dispersed in 5 ml acetone. 0.2 ml triethylamine was added to the dispersion as was 0.2 ml of tolylene-2,4-diisocyanate. After 30 minutes, the beads were washed with acetone and then an acetate buffer at pH 4.75. Five (5) ml of glucoamylase solution (25 mg/ml) were added. The enzyme was thereby immobilized on the beads with an activity of 2,000 units/gm cellulose beads.

EXAMPLE VIII

Two hundred (200) mg glucose isomerase in maleic acid buffer solution was immobilized onto 2 gm of cellulose beads by the same procedure as described in Example VII. The cellulose beads contained 90 units of enzyme activity per gm of cellulose beads at 60° C. using 9% fructose as the substrate.

EXAMPLE IX

Three hundred (300) mg of invertase in 5 ml of acetate buffer were immobilized onto 0.5 gm of porous cellulose beads using the procedure described in Example VII. The cellulose beads contained 3000 units activity per gm of cellulose used.

EXAMPLE X

Fifty (50) mg of lactase in phosphate buffer (pH = 7.0) were immobilized onto 0.5 gm cellulose beads using the procedure described in Example VI. The resulting cellulose beads contained about 80 units enzyme activity per gm of cellulose beads at 30° C. using 1% lactase as subtrate.

EXAMPLE XI

Five hundred (500) mg of glucose isomerase were dissolved in 150 ml maleic acid buffer (0.01 M, pH = 5.5). The enzyme solution was pumped through 5 gm porous cross-linked cellulose beads prepared as described in Example XVI. The DEAE cellulose beads thus contained 100 units of enzyme activity per gm of beads.

EXAMPLE XII

One-quarter (0.25) gm of porous cellulose beads, produced in accordance with Example I, was soaked in 3% of glutaraldehyde and 0.1 M $MgCl_2$. After drying, using vacuum suction on a Buchner funnel, the samples were heated at 80° C. for 30 minutes. Five (5) ml of glucoamylase (25 mg/ml) were added to the beads. After standing overnight, the beads thus prepared contained about 200 units of enzyme activity per gm of dry cellulose beads.

EXAMPLE XIII

One (1) gm of porous cellulose beads was cyanoethylated with 10 ml acryl nitrite (C=C—C≡N) at 50° C. The so-treated cellulose beads were then treated with hydroxylamine at a pH 6.5–6.7 at 50°–100° C. for 4 hours. The resulting modified porous bead product contained

groups and is suitable for absorbing heavy ions such as ferric, ferrous and cupric.

EXAMPLE XIV

A suspension of 2.5 gm porous cellulose beads was treated with 2.5 ml hexamethylene diisocyanate and triethylamine, followed by hydrolysis in water. The product was then treated with 50 ml of 0.5 M O-methylioso-urea at pH>9.5. The product obtained has the following functional group:

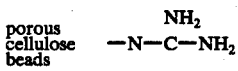

which is useful as an anionic ion exchanger.

EXAMPLE XV

Five (5) grams of porous cellulose beads, obtained according to Example I, were added to 100 ml of 36% formaldehyde and 200 ml of 37% hydrochloric acid. After standing for 1½ hours at room temperature, the beads were filtered and subsequently washed with water and 0.2% sodium carbonate solution. The beads were then dried at 75° to 80° C. The resulting cross-linked porous cellulose beads exhibited strong physical strength.

EXAMPLE XVI

Three (3) grams of porous cellulose beads were cross-linked by formaldehyde according to the process of Example XV. The beads were then treated with 3 grams of 2-chlorotriethylamine. After heating the mixture for a period of 35 minutes at a temperature of 80° to 85° C., the beads were then washed sequentially with sodium chloride, sodium hydroxide, hydrochloric acid, water and ethanol. The cross-linked porous DEAE cellulose beads so obtained exhibited excellent porosity having a void space greater than 50% by volume.

EXAMPLE XVII

A dispersion was formed of 0.5 grams porous cellulose beads in 5 ml of 0.2 N sodium hydroxide and 5 ml epichlorohydrin. The dispersion was then heated for several minutes to a temperature of 80°C. Subsequently, the beads were washed and the cross-linked porous beads so treated exhibited greater strength than the porous cellulose beads prior to cross-linking. Wet cellulose beads, obtained according to the procedure of Example I, were washed in acetone. The washed beads were then suspeneded in dry acetone containing 0.6 ml of triethylamine for each gram of cellulose. Tolylene-2,4-diisocyanate, in an amount of 1.6 ml per gram of cellulose beads, was added to the suspension at 0° C. After a period of 30 minutes, the beads were washed with dry acetone and subsequently filtered. The resulting porous cellulose beads contain isocyanate-reactive groups which could then be hydrolyzed to an amino group by the addition of water.

The invention, in its broader aspects, is not limited to the specific details shown and described, but departures may be made from such details within the scope of the accompanying claims without departing from the principles of the invention. Furthermore, the invention may comprise, consist, or consist essentially, of the hereinbefore-recited materials and steps.

We claim:

1. A process for the preparation of porous cellulose beads suitable for use as a carrier of enzymes and other biological agents which comprises the steps of:
   a. dissolving a hydrolyzable cellulose derivative in an inert organic, water-miscible solvent selected from the group of a mixture of acetone and dimethylsulfoxide and a mixture of acetone and formamide to form a solution having a density greater than that of a precipitation solution the cellulose derivative to solvent ratio ranging from 1:20 to 1:3 weight/volume;
   b. distributing said solution in the form of droplets into a precipitation solution whereby said cellulose derivative is precipitated in the form of uniformly porous beads;
   c. separating the precipitated beads from said solution;
   d. washing the separated porous beads with water;
   e. hydrolyzing the washed beads to convert the beads to cellulose and to increase the active sites for attachment of enzymes and other biological agents;
   f. washing the hydrolyzed beads to obtain porous cellulose beads having a uniformly distributed void space greater than 50% by volume.

2. A process according to claim 1 wherein distributing is accomplished by spraying.

3. A process according to claim 1 wherein said precipitation solution is an aqueous solution or liquid aliphatic hydrocarbon.

4. A process according to claim 3 wherein said precipitation solution is water.

5. A process according to claim 1 wherein said cellulose derivative is cellulose acetate and hydrolysis is carried out in a caustic solution.

6. A process according to claim 1 wherein the void space of said beads is from about 75 to 95%.

7. A process according to claim 1 wherein said porous cellulose beads are cross-linked with at least one cross-linking agent to obtain cross-linked porous cellulose beads.

8. A process according to claim 7 wherein said beads are cross-linked prior to being hydrolyzed.

9. A process according to claim 7 wherein said beads are cross-linked after being hydrolyzed.

10. A process according to claim 7 wherein said cross-linking agent is a diisocyanate.

11. A process according to claim 10 wherein said diisocyanate is tolylene-2,4-diisocyanate or hexamethylene diisocyanate.

12. A process according to claim 7 wherein said cross-linking agent is epichlorohydrin in a sodium hydroxide solution.

13. A process according to claim 7 wherein said cross-linking agent is formaldehyde in a hydrochloric acid solution.

14. A process according to claim 7 wherein said cross-linking agent is glutaraldehyde.

15. A process according to claim 1 wherein said cellulose derivative is cellulose acetate.

16. A process according to claim 15 wherein said inert organic, water-miscible solvent is a mixture of acetone and dimethylsulfoxide.

17. A process according to claim 16 wherein the ratio by volume of acetone to dimethylsulfoxide is 6 to 4.

18. A process according to claim 15 wherein said inert organic water-miscible solvent is a mixture of acetone and formamide.

19. A process according to claim 18 wherein the volume ratio of acetone to formamide is 7 to 3.

20. A process according to claim 1 wherein said porous cellulose beads are at least 0.11 mm in diameter.

21. Porous spherical cellulose beads produced according to the process of claim 1.

22. Porous cross-linked spherical cellulose beads produced according to the method of claim 7.

* * * * *